(12) United States Patent
Fernald (10) Patent No.: US 9,498,282 B2
(45) Date of Patent: Nov. 22, 2016

(54) MEDICAL PROBE WITH ECHOGENIC AND INSULATIVE PROPERTIES

(75) Inventor: Kathleen Fernald, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1881 days.

(21) Appl. No.: 12/028,329

(22) Filed: Feb. 8, 2008

(65) Prior Publication Data

US 2009/0005774 A1 Jan. 1, 2009

Related U.S. Application Data

(60) Provisional application No. 60/889,222, filed on Feb. 9, 2007.

(51) Int. Cl.
*A61B 18/14* (2006.01)
*A61L 31/18* (2006.01)
*A61B 18/00* (2006.01)

(52) U.S. Cl.
CPC ......... *A61B 18/148* (2013.01); *A61B 18/1482* (2013.01); *A61B 18/1485* (2013.01); *A61L 31/18* (2013.01); *A61B 34/20* (2016.02); *A61B 2018/00083* (2013.01); *A61B 2018/00196* (2013.01); *A61B 2018/00577* (2013.01); *A61B 2090/3925* (2016.02)

(58) Field of Classification Search
CPC .................. A61B 18/1482; A61B 2018/00083
USPC .................................. 606/28–29, 33–34, 41
See application file for complete search history.

(56) References Cited

U.S. PATENT DOCUMENTS

| 5,730,742 | A | * | 3/1998 | Wojciechowicz | 606/49 |
| 5,908,385 | A | * | 6/1999 | Chechelski et al. | 600/374 |
| 6,068,626 | A | * | 5/2000 | Harrington et al. | 606/28 |

(Continued)

FOREIGN PATENT DOCUMENTS

| WO | WO 01/57655 A2 | 8/2001 |
| WO | WO 02/30482 A1 | 4/2002 |
| WO | WO 2004/020024 A1 | 3/2004 |

OTHER PUBLICATIONS

PCT International Search Report for PCT/US2008/053478, Applicant: Boston Scientific Scimed, Inc., Form PCT/ISA/210 and 220, dated Jul. 15, 2008 (6 pages).

(Continued)

*Primary Examiner* — Joseph Stoklosa
*Assistant Examiner* — Thomas Giuliani (57) ABSTRACT

Tissue ablation probes and methods of using tissue ablation probes are provided. Each tissue ablation probe comprises an electrically conductive probe shaft, at least one tissue ablation electrode carried by a distal end of the probe shaft, and one or both of an insulative element and an echogenic element. The insulative element and/or the echogenic element may, e.g., be affixed to, or selectively removable from, the probe shaft to increase the insulative capability and echogenicity of the probe. An echogenic sheath having the insulative element and/or the echogenic element may be slidably disposed over the probe shaft to impart insulative and echogenic properties to the probe shaft.

12 Claims, 9 Drawing Sheets

(56) References Cited

U.S. PATENT DOCUMENTS

| | | | |
|---|---|---|---|
| 6,379,353 B1* | 4/2002 | Nichols | 606/41 |
| 6,485,489 B2* | 11/2002 | Teirstein et al. | 606/41 |
| 6,506,156 B1* | 1/2003 | Jones et al. | 600/439 |
| 2001/0034514 A1* | 10/2001 | Parker | 604/525 |
| 2001/0047167 A1* | 11/2001 | Heggeness | 606/41 |
| 2002/0032441 A1* | 3/2002 | Ingle et al. | 606/41 |
| 2003/0199887 A1 | 10/2003 | Ferrera et al. | |
| 2004/0002699 A1 | 1/2004 | Ryan et al. | |
| 2004/0267251 A1 | 12/2004 | Sutton | |
| 2006/0084966 A1* | 4/2006 | Maguire et al. | 606/41 |
| 2007/0179575 A1* | 8/2007 | Esch et al. | 607/96 |
| 2008/0009852 A1 | 1/2008 | Fernald et al. | |

OTHER PUBLICATIONS

PCT Written Opinion of the International Search Authority for PCT/US2008/053478, Applicant: Boston Scientific Scimed, Inc., Form PCT/ISA/237, dated Jul. 15, 2008 (6 pages).

PCT International Preliminary Report on Patentability (Chapter I of the Patent Cooperation Treaty) for PCT/US2008/053478, Applicant: Boston Scientific Scimed, Inc., Form PCT/IB/326 and 373, dated Aug. 11, 2009 (7 pages).

* cited by examiner

MEDICAL PROBE WITH ECHOGENIC AND INSULATIVE PROPERTIES

CROSS-REFERENCE TO RELATED APPLICATIONS

The present application claims the benefit under 35 U.S.C. §119 to U.S. Provisional Patent Application Ser. Nos. 60/889,222, filed on Feb. 9, 2007. The foregoing application is hereby incorporated by reference into the present application in its entirety.

FIELD OF THE INVENTION

The field of the invention relates generally to the structure and use of medical probes, for example ablation probes, for the treatment of tissue.

BACKGROUND OF THE INVENTION

The delivery of radio frequency (RF) energy to target regions within solid tissue is known for a variety of purposes of particular interest to the invention. In one particular application, RF energy may be delivered to diseased regions (e.g., tumors) for the purpose of ablating predictable volumes of tissue with minimal patient trauma.

RF ablation of tumors is currently performed using one of two core technologies. The first technology uses a single needle electrode, which when attached to a RF generator, emits RF energy from an exposed, uninsulated portion of the electrode. The second technology utilizes multiple needle electrodes, which have been designed for the treatment and necrosis of tumors in the liver and other solid tissues. U.S. Pat. No. 6,379,353 discloses such a probe, referred to as a LeVeen Needle Electrode™, which comprises a cannula and an electrode deployment member reciprocatably mounted within the delivery cannula to alternately deploy an electrode array from the cannula and retract the electrode array within the cannula. Using either of the two technologies, the energy that is conveyed from the electrode(s) translates into ion agitation, which is converted into heat and induces cellular death via coagulation necrosis. The ablation probes of both technologies are typically designed to be percutaneously introduced into a patient in order to ablate the target tissue.

In the design of such ablation probes, which may be applicable to either of the two technologies, RF energy is often delivered to an electrode located on a distal end of the probe's shaft via the shaft itself. This delivery of RF energy requires the probe to be electrically insulated to prevent undesirable ablation of healthy tissue. In the case of a single needle electrode, all but the distal tip of the electrode is coated with electrically insulative material in order to focus the RF energy at the target tissue located adjacent the distal tip of the probe. In the case of a LeVeen Needle Electrode™, RF energy is conveyed to the needle electrodes through the inner electrode deployment member, and the outer cannula is coated with an electrically insulative material to prevent RF energy from being transversely conveyed from the inner electrode deployment member along the length of the probe.

When introducing an ablation probe within a patient to treat target tissue, it is desirable that the distal end of the ablation probe, where the RF energy will be directed, is in contact with the target tissue. This may be achieved by visualizing the ablation probe with an imaging device located outside the patient's body, such as an ultrasound imager. The echogenicity of the probe determines how efficiently and accurately the probe may be located using ultrasound techniques. That is, the more echogenetic the ablation probe, the easier it is to determine the location of the probe with ultrasound imaging and to ensure accurate contact with the target tissue.

While echogenicity of a probe may be desired, a user is nonetheless limited to the capabilities the probe has after it is manufactured and shipped. Thus, a probe lacking suitable echogenicity may not be easily visualized with an imaging device during a tissue ablation procedure, making the ablation procedure more difficult. In another situation, a user may obtain a probe from a manufacturer without expecting a need for having an echogenic probe, but changed circumstances may require additional echogenicity of the probe.

Therefore, there is a need in the art for a medical probe with increased echogenicity. There is also a need in the art for providing a user the capability of increasing the echogenicity of a probe after it has been manufactured and shipped.

SUMMARY OF THE INVENTION

In accordance with one embodiment of the inventions, a medical probe comprises a rigid probe shaft, and at least one operative element (e.g., an electrode) associated with the probe shaft, and a thread arrangement disposed over the shaft, wherein the echogenicity of the probe is increased by the thread arrangement. The thread arrangement may be composed of any material that provides echogenic qualities, such as metal, and may take in any suitable form, such as, e.g., a thread wound in a helix arrangement, a plurality of threads wound in a double-helix arrangement, or a plurality of threads in a mesh arrangement. In one embodiment, the probe further comprises an electrically insulative sheath, in which case, the thread arrangement may be disposed over the thread arrangement, underneath the insulative sheath, or embedded within the insulative sheath.

In accordance with another embodiment of the inventions, a medical probe comprises an electrically conductive probe shaft, which may be rigid, semi-rigid, or flexible, at least one electrode (e.g., a tissue ablation electrode) carried by the distal end of the probe shaft, and an electrical connector carried by the proximal end of the probe shaft and electrically coupled to the electrode(s) through the probe shaft. An electrically insulative layer is disposed over the probe shaft, and a thread arrangement disposed over the probe shaft, wherein the echogenicity of the probe is increased by the thread arrangement. The arrangement and specific features of the thread arrangement and insulative layer may be the same as the insulative layer and thread arrangement described above.

In accordance with yet another embodiment of the inventions, a medical probe assembly comprises an electrically conductive probe shaft, which may be rigid, semi-rigid, or flexible, at least one electrode (e.g., a tissue ablation electrode) carried by the distal end of the probe shaft, and an electrical connector carried by the proximal end of the probe shaft and electrically coupled to electrode(s) through the probe shaft. The medical probe assembly further comprises an echogenic sheath slidably disposed on the probe shaft. The sheath has a sheath body and a thread arrangement carried by the sheath body, wherein the echogenicity of the probe is increased by the thread arrangement. In an optional embodiment, the sheath is electrically insulative. The specific features of the thread arrangement may be the same as the thread arrangement described above.

In accordance with yet another embodiment of the inventions, a medical probe assembly comprises a rigid probe shaft, at least one operative element (e.g., an electrode) associated with the probe shaft, and an echogenic sheath slidably disposed on the probe shaft. The sheath has a sheath body and a thread arrangement carried by the sheath body, wherein the echogenicity of the probe is increased by the thread arrangement. In an optional embodiment, the sheath is electrically insulative. The details of the thread arrangement may be the same as the thread arrangement described above.

In accordance with still another embodiment of the inventions, an echogenic sheath configured for being slidably disposed over the shaft of a percutaneous medical probe is provided. The echogenic sheath comprises an elongated sheath body, and one or more echogenic elements (e.g., a thread arrangement) carried by the sheath body, wherein the echogenicity of the medical probe is increased when the sheath is slid over the shaft of the medical probe. In one embodiment, the sheath body is electrically insulative. A medical probe assembly may comprise a percutaneous medical probe and the sheath disposed over the medical probe.

In accordance with a still further embodiment of the inventions, a medical probe assembly comprises a rigid medical probe (e.g., a tissue ablation probe), and an echogenic sheath slidably disposed over the medical probe.

In accordance with yet another embodiment of the inventions, methods of using the foregoing medical probes and medical probe assemblies are provided, including methods of introducing the previously described medical probe into a patient. In this case of a rigid probe, the probe can be percutaneously introduced into the patient. The methods further comprise ultrasonically imaging the medical probe to locate the medical probe, operative element, or electrode, adjacent a tissue region, and operating the medical probe to perform a medical function. If the operative element is an electrode, electrical energy may be conveyed to or from the electrode to treat the patent. If a medical probe assembly is used, a user at a medical facility can slide the sheath over the probe.

BRIEF DESCRIPTION OF THE DRAWINGS

The drawings illustrate the design and utility of illustrated embodiments of the invention, in which similar elements are referred to by common reference numerals. In order to better appreciate how the above-recited and other advantages of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE ILLUSTRATED EMBODIMENTS

Figure 1:
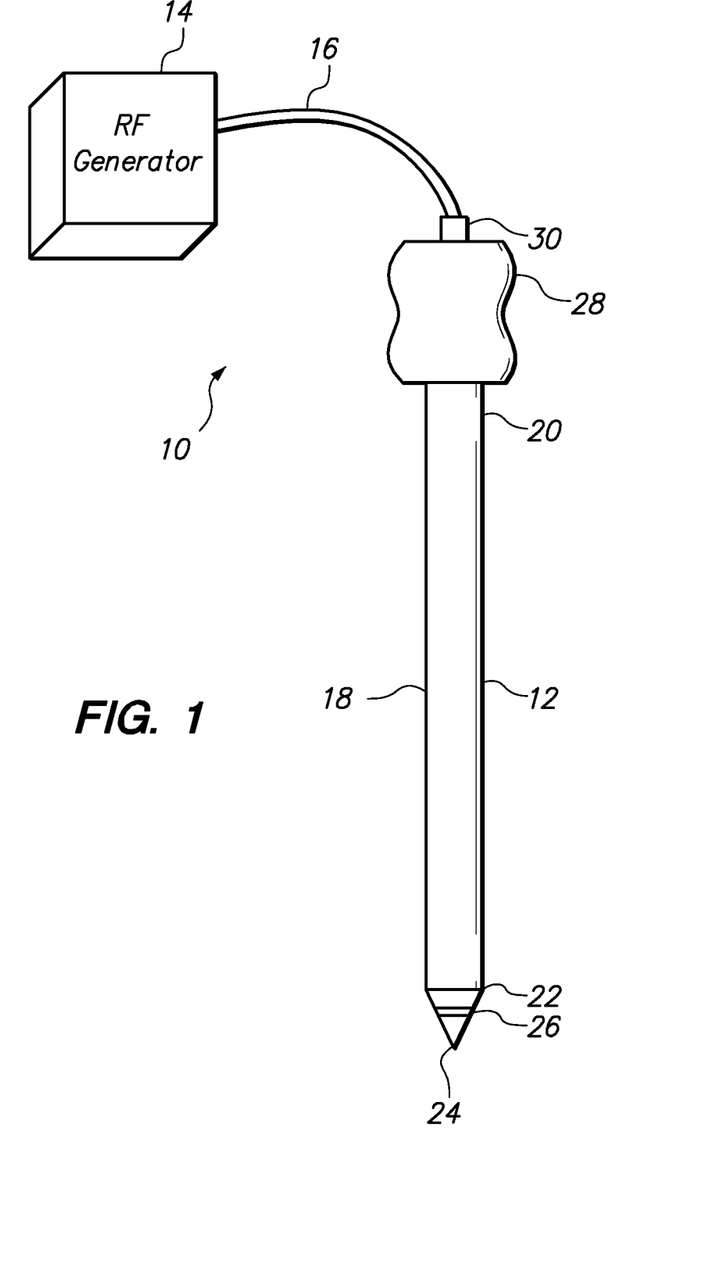
FIG. 1 is a plan view of a tissue ablation system arranged in accordance with one embodiment of the inventions.

Referring to FIG. 1, a tissue ablation system 10 constructed in accordance with one embodiment of the inventions, will now be described. The tissue ablation system 10 generally comprises an ablation probe 12 configured for introduction into the body of a patient for ablative treatment of target tissue, a source of ablation energy, and in particular a radio frequency (RF) generator 14, and a cable 16 electrically connecting the ablation probe 12 to the RF generator 14.

The RF generator 14 may be a conventional general purpose electrosurgical power supply operating at a frequency in the range from 300 kHz to 9.5 MHz, with a conventional sinusoidal or non-sinusoidal wave form. Such power supplies are available from many commercial suppliers, such as Valleylab, Aspen, Bovie, and Ellman. Most general purpose electrosurgical power supplies, however, are constant current, variable voltage devices and operate at higher voltages and powers than would normally be necessary or suitable. Thus, such power supplies will usually be operated initially at the lower ends of their voltage and power capabilities, with voltage then being increased as necessary to maintain current flow. More suitable power supplies will be capable of supplying an ablation current at a relatively low fixed voltage, typically below 200 V (peak-to-peak). Such low voltage operation permits use of a power supply that will significantly and passively reduce output in response to impedance changes in the target tissue. The output will usually be from 5 W to 300 W, usually having a sinusoidal wave form, but other wave forms would also be acceptable. Power supplies capable of operating within these ranges are available from commercial vendors, such as Boston Scientific Corporation. Preferred power supplies are models RF-2000 and RF-3000, available from Boston Scientific Corporation.

The ablation probe 12 comprises an elongated, rigid probe shaft 18 having a proximal end 20 and a distal end 22. For the purposes of this specification, a shaft of a probe is rigid if it is generally not suitable to be advanced along a tortuous anatomical conduit of a patient, as contrasted to, e.g., guidewires and intravascular catheters. The probe shaft 18 has a suitable length, typically in the range from 5 cm to 30 cm, preferably from 10 cm to 25 cm, and an outer diameter consistent with its intended use, typically being from 0.7 mm to 5 mm, usually from 1 mm to 4 mm. In the illustrated embodiment embodiment, the probe shaft 18 is composed of an electrically conductive material, such as stainless steel. The distal end 22 of the probe shaft 18 includes a tissue-penetrating distal tip 24, which allows the ablation probe 12 to be more easily introduced through tissue, while minimizing tissue trauma.

The tissue ablation probe further comprises an electrode 26 carried on the distal end 22 of the probe 12 for application in a medical procedure. In the illustrated embodiment, the electrode 26 is an RF ablation electrode 26 formed by the distal tip 24. In alternative embodiments, the electrode 26 may be a discrete element that is mounted to the distal tip 24 via suitable means, such as bonding or welding.

The ablation probe 12 further comprises a handle 28 mounted to the proximal end 20 of the probe shaft 18. The handle 28 is preferably composed of a durable and rigid material, such as medical grade plastic, and is ergonomically molded to allow a physician to more easily manipulate the ablation probe 12. The handle 28 comprises an electrical connector 30 with which the cable 16 (shown in FIG. 1) mates. Alternatively, the RF cable 16 may be hardwired within the handle 28. The electrical connector 30 is electrically coupled to the ablation electrode 26 via the probe shaft 18.

In the illustrated embodiment, the RF current is delivered to the electrode 26 in a monopolar fashion, which means that current will pass from the electrode 26, which is configured to concentrate the energy flux in order to have an injurious effect on the surrounding tissue, and a dispersive electrode (not shown), which is located remotely from the electrode 26 and has a sufficiently large area (typically 130 cm2 for an adult), so that the current density is low and non-injurious to surrounding tissue. The dispersive electrode may be attached externally to the patient, e.g., using a contact pad placed on the patient's flank.

In an alternative embodiment, two electrodes 26 may be carried on the distal end 22 in a bipolar fashion. Thus, when the RF energy is conveyed to the electrodes, the RF current passes between the electrodes; i.e., between a positive one of the electrodes and a negative one of the electrodes, thereby concentrating the energy flux in order to have an injurious effect on the tissue between the electrodes. In this bipolar arrangement, the electrodes 26 will have to be electrically insulative from each other, in which case, the electrical connector 30 may be coupled to one or both of the electrodes 26 via separate wires, instead of through the probe shaft 18.

Figure 2:
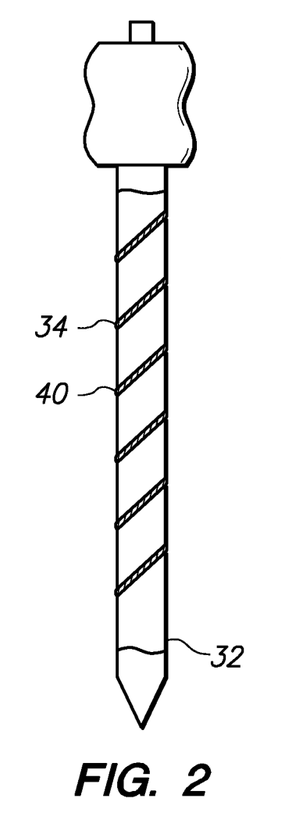
FIG. 2 is a side view of one embodiment of a tissue ablation probe that can be used in the tissue ablation system of FIG. 1.
Figure 3:
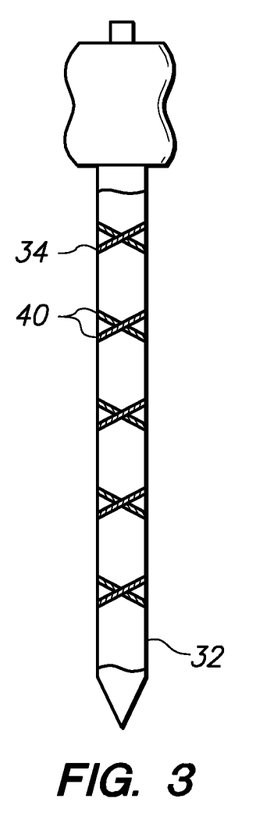
FIG. 3 is a side view of another embodiment of a tissue ablation probe that can be used in the tissue ablation system of FIG. 1.
Figure 4:
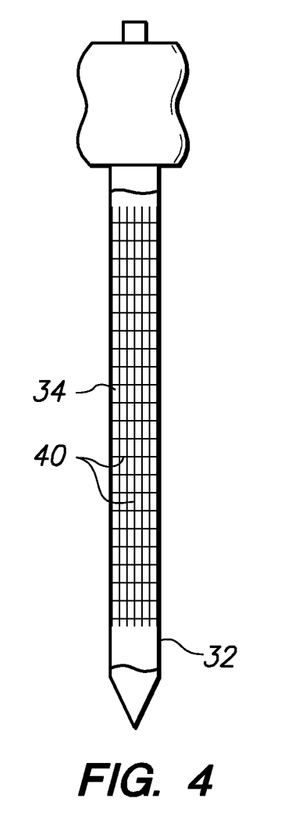
FIG. 4 is a side view of still another embodiment of a tissue ablation probe that can be used in the tissue ablation system of FIG. 1.

Referring further to FIGS. 2-4, the ablation probe 12 also comprises an electrically insulative layer 32 disposed on the probe shaft to impart an insulative property to the shaft 18. The insulative layer 32 comprises any material suited for its purpose, such as polyether ether ketone (PEEK) or fluorinated ethylene-propylene (FEP). Preferably, the insulative layer 32 is sized to cover most of the probe shaft 18, thereby focusing all of the RF energy at the electrode 26 where the targeted tissue presumably lies, while preventing the RF energy conducted through the shaft 18 from damaging healthy tissue surrounding the shaft 18 away from the electrode 32.

The ablation probe 12 further comprises an echogenic element, and in particular a thread arrangement 34, disposed on the probe shaft 18 to impart echogenic properties to the probe shaft 18. The echogenic element 34 may be affixed to the probe shaft 18 or the insulative layer 32. The echogenic element 34 embodies a form that varies the surface profile of the probe shaft 18, thus increasing the echogenicity of the probe 12.

Figure 2A:
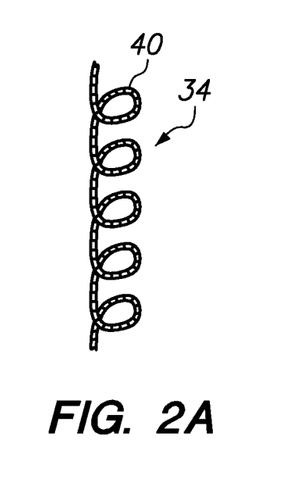
FIG. 2A is a perspective view of a thread arrangement used to increase the echogenicity of the tissue ablation probe of FIG. 2.
Figure 3A:
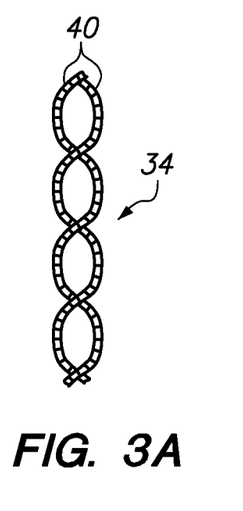
FIG. 3A is a perspective view of a thread arrangement used to increase the echogenicity of the tissue ablation probe of FIG. 3.
Figure 4A:
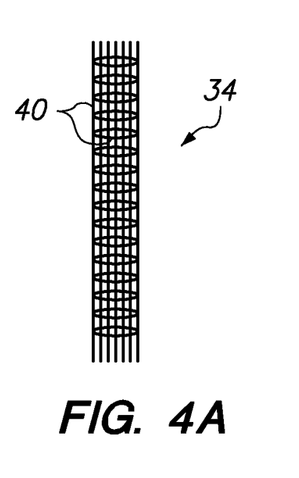
FIG. 4A is a perspective view of a thread arrangement used to increase the echogenicity of the tissue ablation probe of FIG. 4.

For example, the thread arrangement 34 may comprise: a single thread 40 wound in a helix formation over the probe shaft 18 (FIGS. 2 and 2A); two threads 40 wound in a double-helix formation over the probe shaft 18 (FIGS. 3 and 3A); or a plurality of threads 40 in a screen or mesh arrangement over the probe shaft 18 (FIGS. 4 and 4A). While the embodiment comprising a single thread 40 wound in a helical arrangement may sufficiently vary the surface profile of the probe shaft 18 to increase its echogenicity, the embodiments comprising multiple threads 40, such as the double-helical and screen arrangements, may further increase echogenicity by further varying the surface profile.

The form of the thread arrangement 34 selected may depend on the procedure for which the probe 12 is used. For example, some ablation procedures may only require the probe 12 to have a moderate level of echogenicity, for example, an ablation procedure in an anatomical vessel, such as a bronchial tube, in which the target tissue is located fairly easily. In this case, it may be preferable to have a thread arrangement 34 on the probe 12 comprising a helical or double-helical arrangement. This may allow for greater ease in percutaneously inserting the probe 12 into the patient, while still imparting an elevated level of echogenicity. For an ablation procedure taking place within a more concentrated mass of tissue, for example, within liver tissue, a higher level of echogenicity may be desired, such that a mesh arrangement of the thread arrangement 34 would be preferred.

The thread(s) 40 may be composed of one or more materials, particularly flexible materials, suited for its purpose, such as: metal, including stainless steel or copper; plastic or other polymeric materials; natural or synthetic fibers; and combinations thereof. Additionally, in the thread arrangements 34 having multiple threads 40, each thread 40 may be comprised of different materials. The thread(s) 40 may have other features that further increase echogenicity, such as bubbles or nicks in the thread(s) 40, or echogenic particles disposed on the thread(s) 40. In addition to the thread arrangement 34, other forms of echogenic elements that vary the surface profile and density profile of the probe shaft may be used with the probe 12 and integrated with the insulative layer 32.

Figures 5, 6:
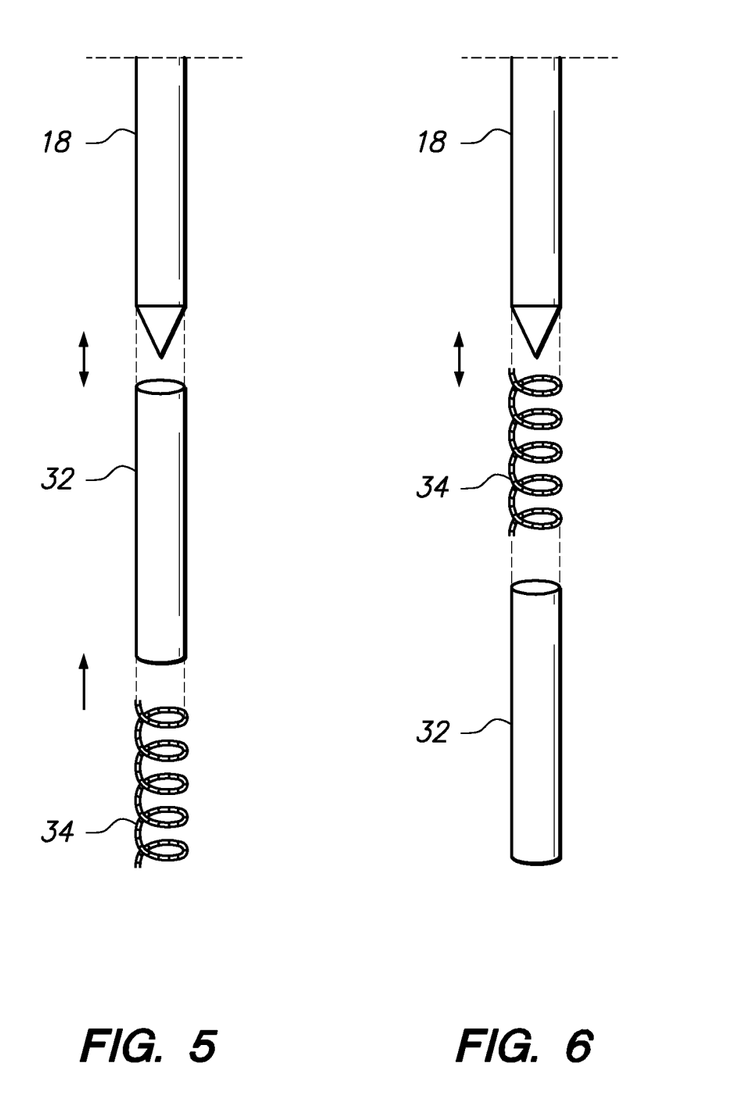
FIG. 5 is an exploded view of the tissue ablation probe of FIG. 2, particularly showing one manner of associating an electrically insulative layer and the thread arrangement with the shaft of the probe.
FIG. 6 is an exploded view of the tissue ablation probe of FIG. 2, particularly showing another manner of associating an electrically insulative layer and the thread arrangement with the shaft of the probe.

The insulative layer 32 and the thread arrangement 34 may be applied to the probe shaft 18 using any suitable means. For example, the insulative layer 32 may be applied as a heat shrink, extruded onto the probe shaft 18, or coated onto the probe shaft, e.g., by dipping the probe shaft 18 into an electrically insulative and liquid material. The thread arrangement 34 may be affixed to the probe shaft 18 with a medical grade adhesive. The positional relationship between the thread arrangement 34 and insulative layer 32 may vary. For example, as illustrated in FIG. 5, the thread arrangement 34 may be disposed over the insulative layer 32. Alternatively, as shown in FIG. 6, the insulative layer 32 may be disposed over the thread arrangement 34. In yet another embodiment, the thread arrangement 34 may be embedded within the insulative layer 32; for example, by extruding the insulative layer 32 with the thread arrangement 34, or by disposing the thread arrangement 34 between two insulative layers 32. In still another embodiment, the insulative layer 32 may be disposed between two layers of the thread arrangement 34.

Figure 7:
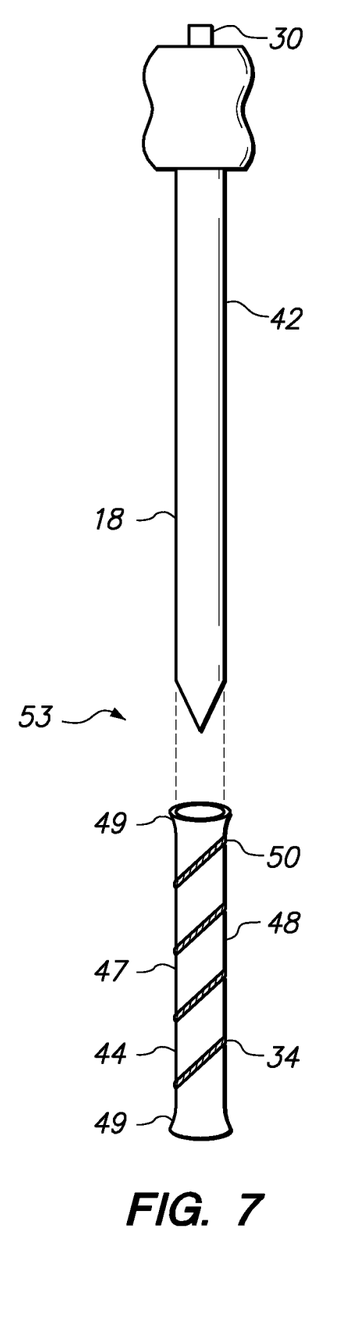
FIG. 7 illustrates a perspective view of one embodiment of a tissue ablation probe assembly that can be used with the tissue ablation system of FIG. 1.

Referring to FIG. 7, a tissue ablation probe assembly 53, instead of the tissue ablation probe 12, can be used in the tissue ablation system 10. The tissue ablation probe assembly 53 generally comprises an ablation probe 42 and an echogenic sheath 44. The tissue ablation probe 42 is similar to that previously described tissue ablation probe 12 in that it comprises the probe shaft 18, electrode 26, and handle 30, but differs in that it does not have an insulative layer bonded to the probe shaft 18.

The echogenic sheath 44 comprises an elongated sheath body 48 that is preferably sized to be slidably disposed on the probe shaft 18. In one embodiment, as illustrated in FIG. 7, the sheath body 48 is cylindrical, having an inner diameter approximately equal to the outer diameter of the probe shaft 18. The sheath body 48 may also have end portions 49 of a greater diameter than a middle portion 47 of the sheath body 48 to facilitate introduction of the echogenic sheath 44 over the probe shaft 18.

The sheath body 48 is composed of a material suited to secure the echogenic sheath 44 over the probe shaft 18. In one embodiment, the sheath body 48 is composed of an electrically insulative material, such as a plastic, elastomer, or ceramic. Thus, the echogenic sheath 44 may be multifunctional in that it imparts both electrically insulative and echogenic properties to the probe 42. This may be especially beneficial when the echogenic sheath 44 is used with a probe that lacks an insulative component sufficient for its use.

Figures 8, 9, 10:
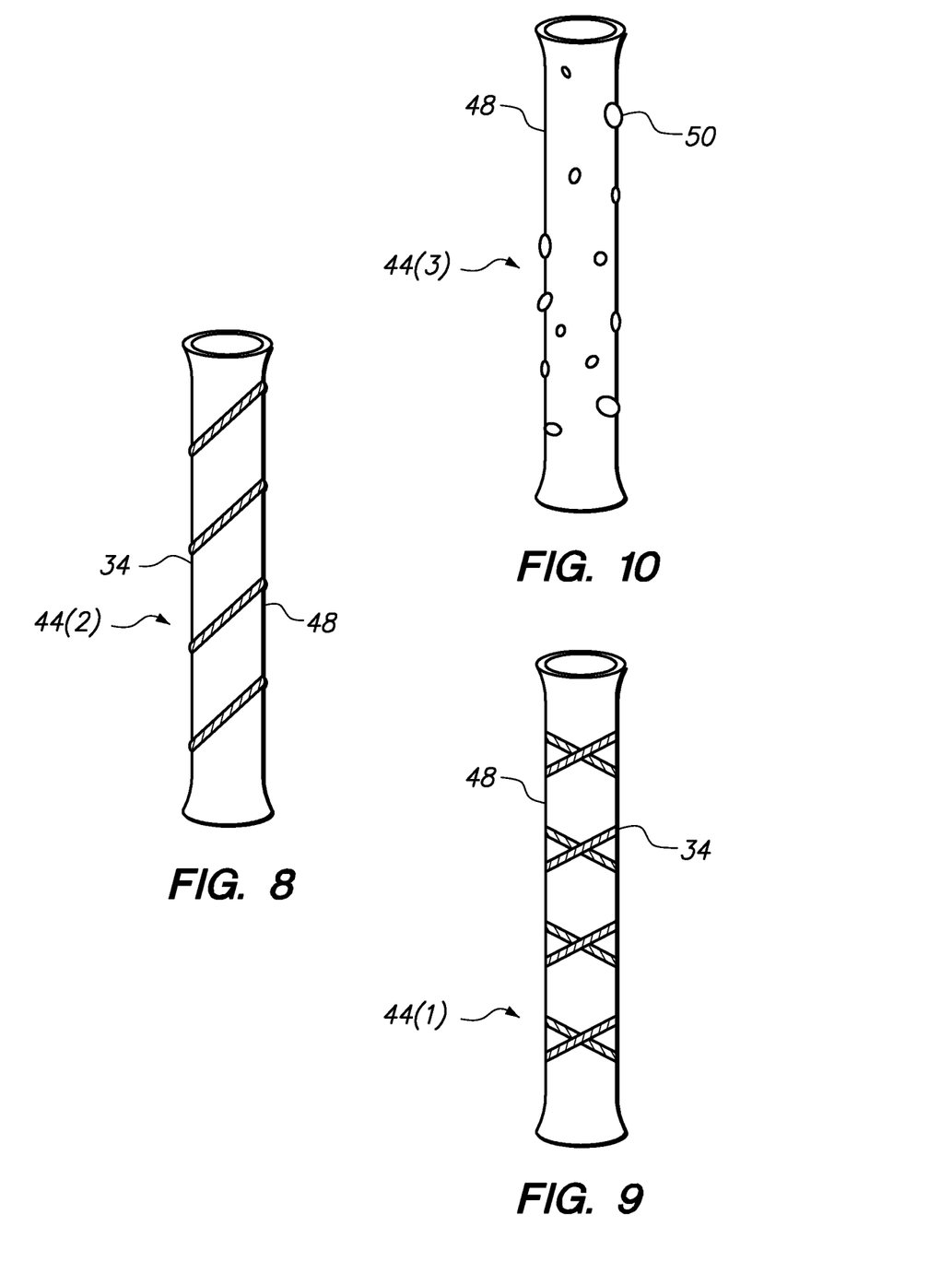
FIG. 8 is a perspective view of an alternative removable echogenic sheath that can be used with the tissue ablation probe assembly of FIG. 7.
FIG. 9 is a perspective view of an another alternative removable echogenic sheath that can be used with the tissue ablation probe assembly of FIG. 7.
FIG. 10 is a perspective view of an another alternative removable echogenic sheath that can be used with the tissue ablation probe assembly of FIG. 7.

The echogenic sheath 44 further comprises one or more echogenic elements 50 integrated with the sheath body 34. In the illustrated embodiment, the echogenic element(s) 50 include the previously described thread arrangement 34. In one embodiment, the thread arrangement 34 is affixed to an outer surface of the echogenic sheath 44, i.e., the surface of the echogenic sheath 44 facing outward from the probe shaft 18, as shown in FIG. 7. Alternatively, as illustrated in FIG. 8, the thread arrangement 34 may be affixed to an inner surface of the echogenic sheath 44, namely the surface adjacent to the probe shaft 18, when the echogenic sheath 44 is slid thereon. In another embodiment, the thread arrangement 34 may be embedded within the sheath body 48, as shown in FIG. 9; for example, by extruding the insulative layer 32 with the thread arrangement 34, or by disposing the thread arrangement 34 between two layers of the sheath body 48. In still another embodiment, the sheath body 48 may be disposed between two layers of the thread arrangement 34.

While the echogenic element 34 on the sheath body 48 has been described in regard to the thread arrangement 34, other embodiments of the echogenic element 34 may be employed. For example, the echogenic sheath 44 may comprise echogenic particles 50, such as condensed-phase particles or bubbles, integrated within the sheath body 48 or disposed over an external surface of the sheath body 48, as shown in FIG. 10. The echogenic particles 50 serve to vary the surface and density profiles of the sheath unit 42, serving to increase the echogenicity of the probe 42 when the sheath unit 42 is disposed thereon. Further details regarding the structure and use of echogenic particles to increase the echogenicity of ablation probes are disclosed in U.S. Patent Application Publication No. 2008-0009852, which is expressly incorporated herein by reference.

Figure 11A:
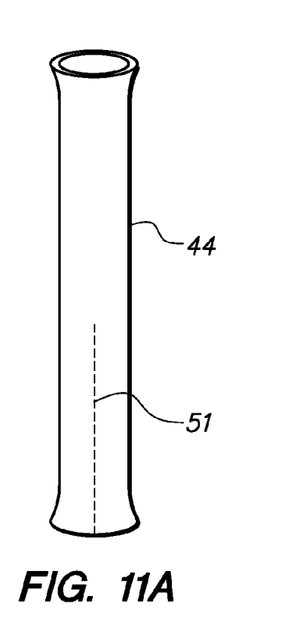
FIGS. 11A and 11B are perspective views of one embodiment of a removable echogenic sheath that can be used with the tissue ablation probe assembly of FIG. 7, particularly shown as being intact and separated.
Figure 11B:
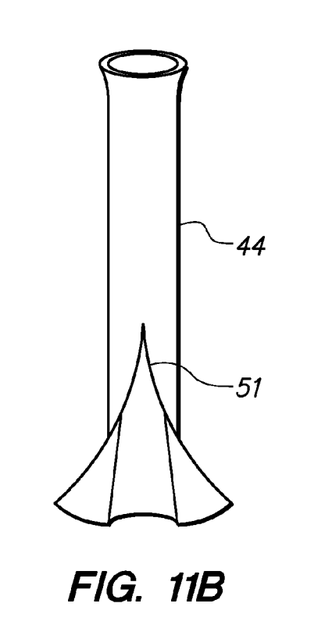

For additional ease in sliding the echogenic sheath 44 over the probe shaft 18, the echogenic sheath 44 may have an opening slit 51 extending over a length of the echogenic sheath 44, as shown in FIG. 11A. The opening slit 51 is selectively separated, as shown in FIG. 11B, to remove or secure the echogenic sheath 44 on the probe shaft 18. The opening slit 51 may then be selectively reattached, for example with a low-tack adhesive on the sheath body 48 along the opening slit 51, to secure the echogenic sheath 44 on the probe shaft 18.

The tissue probe assembly 53 can be distributed from a manufacturer to users at a medical facility, such as a hospital or clinic, with the ablation probe 42 and the echogenic sheath 44 as separate units. The tissue probe assembly 53 thus provides a user with the option of assembling the ablation probe 42 and the echogenic sheath 44 when desired. Additionally, the echogenic sheath 44 may be shipped as a separate unit, i.e., apart from the ablation probe 42, so that it may be applied to other probes requiring additional echogenic and/or insulative capability.

Figure 12:
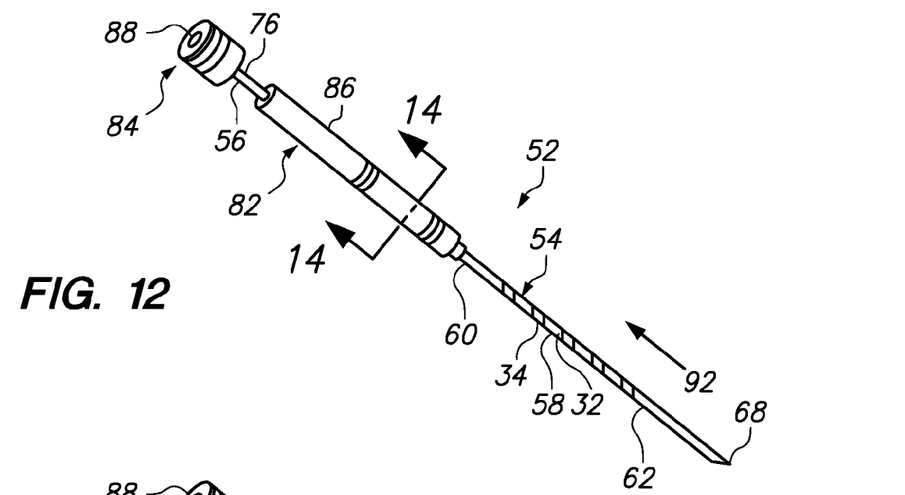
FIG. 12 is a perspective view of another tissue ablation probe that can be used within the tissue ablation system of FIG. 1, wherein an electrode array is particularly shown retracted.
Figures 13, 14:
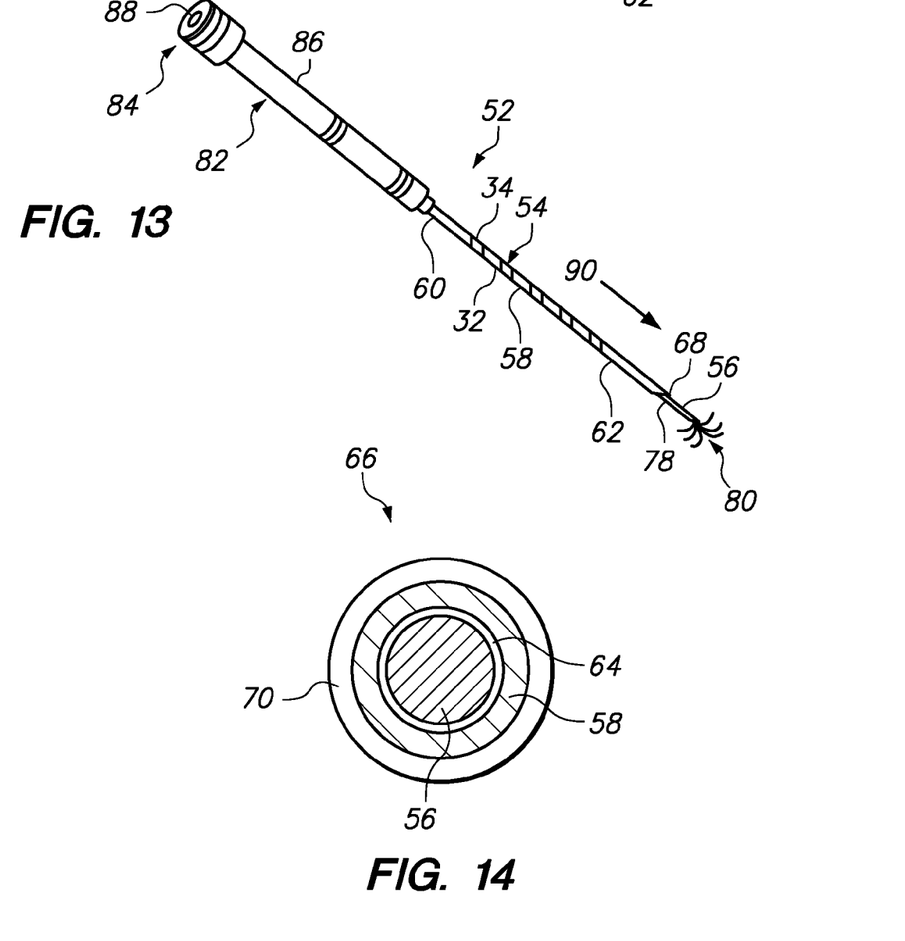
FIG. 13 is a perspective view of the tissue ablation probe of FIG. 12, wherein the electrode array is particularly shown deployed.
FIG. 14 illustrates a cross-sectional views of the tissue ablation probe of FIG. 12, taken along the line 14-14.

Referring now to FIGS. 12 and 13, another tissue ablation probe 52 that can be used in conjunction with the RF generator 14 to create an alternative tissue ablation system will be described. The tissue ablation probe 52 includes an elongated cannula 54 and an inner probe shaft 56 slidably disposed within the cannula 54. The cannula 54 includes an elongate shaft 58 having a proximal end 60, a distal end 62, and a central lumen 64 (shown in FIG. 14).

The cannula shaft 58, itself, is composed of an electrically conductive material, such as stainless steel. The material from which the cannula shaft 58 is composed is preferably a rigid or semi-rigid material, such that the ablation probe 52 can be introduced through solid tissue to a target tissue site. The distal end 62 of the cannula shaft 58 comprises a tissue-penetrating tip 68, which allows the ablation probe 52 to be more easily introduced through tissue, while minimizing tissue trauma. Alternatively, the ablation probe 52 may be introduced through the tissue with the aid of another cannula and trocar assembly, in which case, the cannula shaft 58 may be composed of a flexible material, and the distal end 62 may be blunted. The cannula shaft 58 has a suitable length, typically in the range from 5 cm to 30 cm, preferably from 10 cm to 25 cm, and an outer diameter consistent with its intended use, typically being from 0.7 mm to 5 mm, usually from 1 mm to 4 mm.

The inner probe shaft 56 is slidably disposed within the cannula lumen 64 and has a proximal end 76 and a distal end 78, and an array of electrode tines 80 carried by the distal end 78 of the probe shaft 56. Like the cannula shaft 58, the inner probe shaft 56 is composed of an electrically conductive material, such as stainless steel. The inner probe shaft 56 is composed of a suitably rigid material, so that it has the required axial strength to slide within the cannula lumen 64.

The ablation probe 52 further includes a handle assembly 82, which includes a handle member 84 mounted to the proximal end 76 of the inner probe shaft 56, and a handle sleeve 86 mounted to the proximal end 60 of the cannula 54. The handle member 84 is slidably engaged with the handle sleeve 86 (and the cannula 54). The handle member 84 and handle sleeve 86 can be composed of any suitable rigid material, such as, e.g., metal, plastic, or the like. The handle assembly 82 also includes an electrical connector 88 mounted within the handle member 84. The electrical connector 88 is electrically coupled to the electrode array 80 via the inner probe shaft 56. The electrical connector 88 is configured for mating with the proximal end of the RF cable 16 (shown in FIG. 1). Alternatively, the RF cable 16 may be hardwired within the handle member 84. Like the previously described ablation probe 12, RF current may be delivered to the electrode array 80 in a monopolar fashion.

It may be readily appreciated that longitudinal translation of the probe shaft 56 relative to the cannula 54 in a distal direction 90 can be achieved by holding the handle sleeve 86 and displacing the handle member 84 in the distal direction 90, thereby deploying the electrode array 80 from the distal end 62 of the cannula shaft 58 (FIG. 13), and longitudinal translation of the probe shaft 56 relative to the cannula 54 in a proximal direction 92 can be achieved by holding the handle sleeve 86 and displacing the handle member 84 in the proximal direction 92, thereby retracting the probe shaft 56 and the electrode array 80 into the distal end 62 of the cannula 54 (FIG. 14).

Further details regarding electrode array-type probe arrangements are disclosed in U.S. Pat. No. 6,379,353, which has previously been incorporated herein by reference.

The ablation probe 52 further comprises the previously described insulative layer 32 and thread arrangement 34 disposed on the cannula shaft 58 to impart the desired level of insulative and/or echogenic capability to the ablation probe 52. Alternatively, the above-described echogenic sheath 44 may be slid onto the ablation probe 52 to form a tissue ablation probe assembly (not shown). The echogenic sheath 44 may be used for sliding onto the cannula 54 to impart increased echogenicity and/or insulative capability to the probe 52. It may be appreciated that in this instance, the echogenic sheath 44 may be manufactured and delivered to a user as a separate unit to be slid onto any suitable probe, such as the ablation probe 52 described here, at a desired time.

Having described the structure of the tissue ablation system 10, its operation in treating targeted tissue will now be described. The treatment region may be located anywhere in the body where hyperthermic exposure may be beneficial. Most commonly, the treatment region will comprise a solid tumor within an organ of the body, such as the liver, kidney, pancreas, breast, prostrate (not accessed via the urethra), and the like. The volume to be treated will depend on the size of the tumor or other lesion, typically having a total volume from 1 cm3 to 150 cm3, and often from 2 cm3 to 35 cm3. The peripheral dimensions of the treatment region may be regular, e.g., spherical or ellipsoidal, but will more usually be irregular. The treatment region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor or other lesion being treated, either intraoperatively or externally.

Figure 15A:
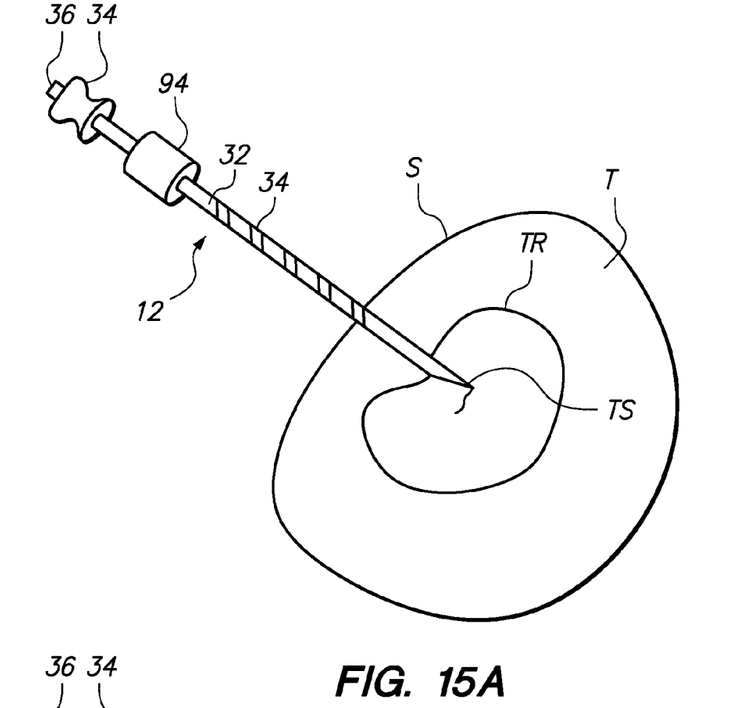
FIGS. 15A-15B illustrate cross-sectional views of one method of using the tissue ablation system of FIG. 1 to treat tissue, wherein the tissue ablation probe of FIG. 2 is particularly used.
Figure 15B:
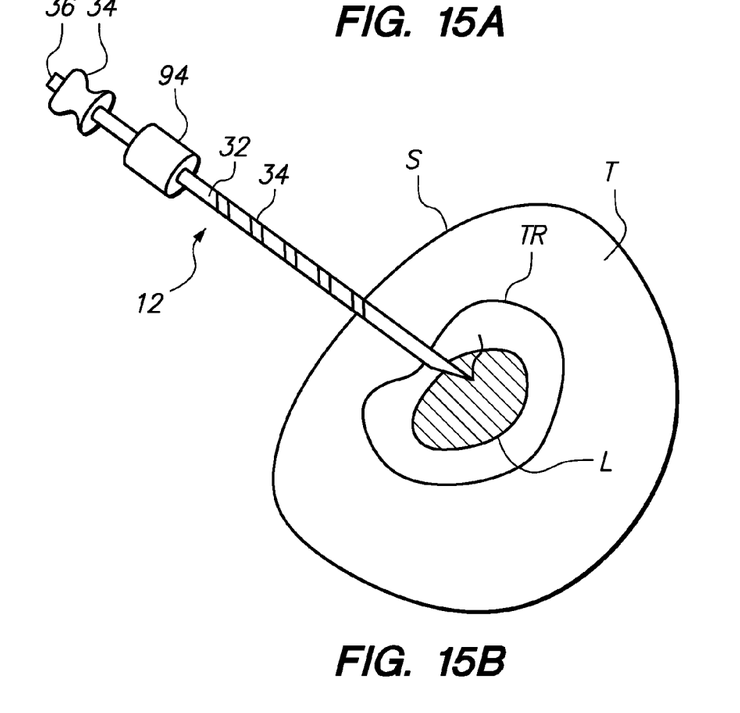

Referring now to FIGS. 15A and 15B, the operation of the tissue ablation system 10 is described in treating a treatment region TR with tissue T located beneath the skin or an organ surface S of a patient. The ablation probe 12 is first introduced through the tissue T under the guidance of a conventional ultrasound imaging device, so that the electrode 26 is located at a target site TS within the treatment region TR, as shown in FIG. 15A. This can be accomplished using any one of a variety of techniques. In the illustrated method, a delivery device, such as a probe guide 94, is used to guide the ablation probe 12 towards the target site TS. In particular, the probe guide 94 is affixed and aligned relative to the target site TS, and the ablation probe 12 is introduced through the probe guide 94. Facilitated by the sharpened distal tip 24, the ablation probe 12 is percutaneously introduced through the patient's skin until the electrode 26 is located in the treatment region TR. During introduction of the ablation probe 12, the insulative layer 32 and the thread arrangement 34 allow the user to more precisely locate the ablation probe 12 during ultrasound imaging, so that the probe 12 is properly positioned for effective ablation of the target tissue.

Once the ablation probe 12 is properly positioned, the cable 16 of the RF generator 14 (shown in FIG. 1) is then connected to the electrical connector 30 of the ablation probe 12, and then operated to transmit RF energy to the electrode 26, thereby ablating the treatment region TR, as illustrated in FIG. 15B. As a result, a lesion L will be created, which will eventually expand to include the entire treatment region TR.

As an alternative to using the tissue ablation probe 12, the tissue probe assembly 53 comprising the ablation probe 42 and the echogenic sheath 44 may be employed in this method of ablating tissue. To be used in this method, the ablation probe assembly 53 is used in the same manner as the ablation probe 12 described above, with the exception that the user must assemble the probe assembly 53. In particular, the ablation probe 42 and the echogenic sheath 44 will be provided to the user as separate units. The user then assembles the tissue probe assembly 53 by sliding the echogenic sheath 44 onto the ablation probe 42, thus increasing the echogenicity of the ablation probe 42. The tissue probe assembly 53 would then be operated with the RF generator to ablate tissue in the same manner as the tissue ablation probe 12.

Figure 16A:
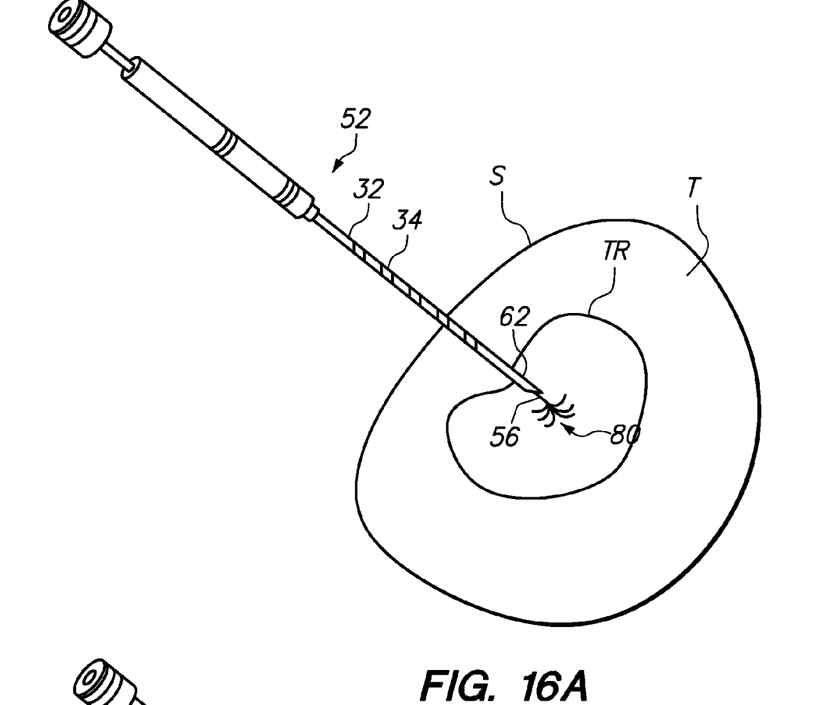
FIGS. 16A-16B illustrate cross-sectional views of another method of using the tissue ablation system of FIG. 1 to treat tissue, wherein the tissue ablation probe of FIG. 12 is particularly used.
Figure 16B:
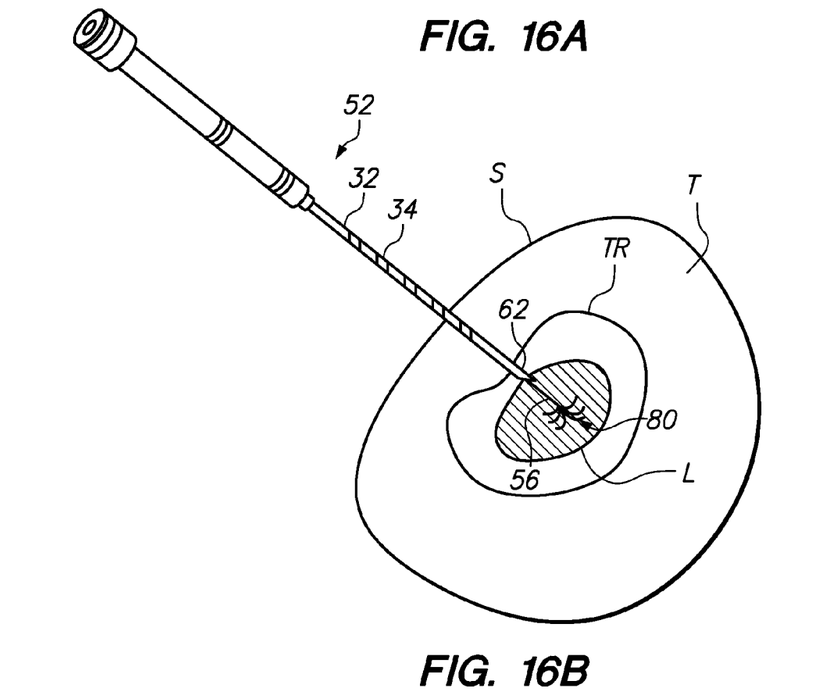

In an alternative method, the ablation probe 52 illustrated in FIGS. 12 and 13 may be used to ablate tissue by introducing the cannula 54 through the probe guide 94 until the distal end 62 of the cannula 54 is located at the target site TS, after which the inner probe shaft 56 can be distally advanced through the cannula 54 to deploy the electrode array 80 out from the distal end 62 of the cannula 54, as shown in FIG. 16A. Again, during introduction of the ablation probe 52, the insulative layer 32 and the thread arrangement 34 allow the user to more precisely locate the ablation probe 52 during ultrasound imaging, so that the probe 52 is properly positioned for effective ablation of the target tissue As previously discussed, once the ablation probe 52 is properly positioned, the cable 16 of the RF generator 14 (shown in FIG. 1) is then connected to the electrical connector 88 of the ablation probe 52, and then operated to transmit RF energy to the electrode array 80, thereby ablating the treatment region TR, as illustrated in FIG. 16B. As a result, a lesion L will be created, which will eventually expand to include the entire treatment region TR.

In an alternate method, the echogenic sheath 44 may be used with the ablation probe 52. In this case, the user slides the echogenic sheath 44 on the ablation probe 52, thus increasing the echogenicity of the probe 52. Afterward, the probe 52 may be operated to ablate tissue, as described above.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A medical probe, comprising:
a rigid probe shaft;
at least one operative medical element associated with the probe shaft; and
an electrically insulative sheath disposed over the probe shaft such that substantially all of an inner surface of the electrically insulative sheath is in contact with an outer surface of the probe shaft, the electrically insulative sheath having a thread arrangement disposed thereon, wherein the echogenicity of the probe shaft is increased by the thread arrangement.

2. The medical probe of claim 1, wherein the thread arrangement is disposed over the insulative sheath.

3. The medical probe of claim 1, wherein the thread arrangement is composed of a metallic material.

4. The medical probe of claim 1, wherein the thread arrangement comprises at least one thread wound in a helix arrangement.

5. The medical probe of claim 1, wherein the thread arrangement comprises a plurality of threads wound in a double-helix arrangement.

6. The medical probe of claim 1, wherein the thread arrangement comprises a plurality of threads in a mesh arrangement.

7. The medical probe of claim 1, wherein the electrically insulative sheath comprises end portions each having a greater diameter than a middle portion.

8. The medical probe of claim 1, wherein the thread arrangement is affixed to an outer surface of the electrically insulative sheath.

9. The medical probe of claim 1, wherein the thread arrangement comprises a polymeric material.

10. The medical probe of claim 1, wherein the probe shaft is made of an electrically conductive material.

11. The medical probe of claim 1, wherein the electrically insulative sheath is sized to cover most of the probe shaft.

12. The medical probe of claim 1, wherein the operative medical element is coupled to a distal end of the probe shaft, and the insulative sheath is disposed over the probe shaft in a position proximal to the operative medical element.

* * * * *